(12) United States Patent
Kashefi-Khorasani et al.

(10) Patent No.: US 10,245,397 B2
(45) Date of Patent: Apr. 2, 2019

(54) DEVICE AND METHOD FOR PERFORMING RESPIRATORY TRAINING

(71) Applicant: Rheinisch-Westfaelische-Technische Hochschule Aachen, Aachen (DE)

(72) Inventors: Ahmad Ali Kashefi-Khorasani, Aachen (DE); Rainer Dautzenberg, Aachen (DE)

(73) Assignee: Rheinisch-Westfaelische-Technische Hochschule Aachen, Aachen (DE)

( * ) Notice: Subject to any disclaimer, the term of this patent is extended or adjusted under 35 U.S.C. 154(b) by 677 days.

(21) Appl. No.: 14/759,131

(22) PCT Filed: Feb. 5, 2014

(86) PCT No.: PCT/EP2014/000305
§ 371 (c)(1),
(2) Date: Jul. 2, 2015

(87) PCT Pub. No.: WO2014/121925
PCT Pub. Date: Aug. 14, 2014

(65) Prior Publication Data
US 2015/0352403 A1 Dec. 10, 2015

(30) Foreign Application Priority Data

Feb. 5, 2013 (DE) .................. 10 2013 001 913

(51) Int. Cl.
*A61M 16/22* (2006.01)
*A61M 16/00* (2006.01)
(Continued)

(52) U.S. Cl.
CPC ........ *A61M 16/0045* (2013.01); *A61M 16/06* (2013.01); *A61M 16/1005* (2014.02);
(Continued)

(58) Field of Classification Search
CPC .............. A61M 16/0045; A61M 16/10; A61M 16/142; A61M 16/145; A61M 16/22; A63B 23/18; A63B 2213/006
See application file for complete search history.

(56) References Cited

U.S. PATENT DOCUMENTS

| 2,969,789 | A | * | 1/1961 | Morch | .................. | A61M 16/00 |
| | | | | | | 128/205.14 |
| 3,489,144 | A | * | 1/1970 | Dibelius | .................. | A62B 7/00 |
| | | | | | | 128/205.12 |

(Continued)

FOREIGN PATENT DOCUMENTS

FR 3046549 A1 * 7/2017 ........... B01D 53/047

*Primary Examiner* — Kathryn E Ditmer
(74) *Attorney, Agent, or Firm* — Andrew Wilford (57) ABSTRACT

The invention relates to a device for performing respiratory training, in particular altitude training, comprising a mouthpiece (1) through which a person can exhale respiratory gas into a volume (2, 3a, 7) or can inhale it out of the volume (2, 3a, 7), wherein this volume (2, 3a, 7) is formed at least in part by a container (2) which is adjustable in terms of its volume and which is connected to the mouthpiece, wherein the volume (2, 3a, 7) adjoins one side of at least one gas-permeable membrane (4), to the other side of which at least one gas exchange chamber (3b) is connected, through which a fluid provided for the gas exchange, in particular $CO_2$ and/or $O_2$ gas exchange, can actively flow. Furthermore, the invention also relates to a method for performing respiratory training, in particular altitude training, wherein a person exhales into a training device through a mouthpiece (1) and inhales from this training device, wherein the $O_2$ and/or $CO_2$ partial pressure in the respiratory gas inhaled from the device is influenced by exchange of $O_2$ and/or $CO_2$ between the respiratory gas in the training device and a fluid provided for the gas exchange through at least one gas-permeable membrane (4).

8 Claims, 8 Drawing Sheets

(51) Int. Cl.
*A61M 16/10* (2006.01)
*A63B 23/18* (2006.01)
*A61M 16/06* (2006.01)
*A61M 16/20* (2006.01)

(52) U.S. Cl.
CPC .......... *A61M 16/208* (2013.01); *A61M 16/22* (2013.01); *A63B 23/18* (2013.01); *A61M 16/107* (2014.02); *A61M 2202/0225* (2013.01); *A61M 2205/17* (2013.01); *A61M 2205/7536* (2013.01); *A63B 2213/006* (2013.01)

(56) References Cited

U.S. PATENT DOCUMENTS

| | | | | |
|---|---|---|---|---|
| 3,674,022 A * | 7/1972 | Dounoucos | ............ | B64D 10/00 128/205.27 |
| 3,910,780 A * | 10/1975 | Henley | ................. | B01D 53/22 96/12 |
| 4,473,082 A * | 9/1984 | Gereg | .................... | A63B 23/18 128/205.17 |
| 4,811,732 A * | 3/1989 | Hartung | ................ | A61M 16/00 128/204.26 |
| 4,898,167 A * | 2/1990 | Pierce | ............... | A61M 16/0075 128/205.11 |
| 5,313,938 A * | 5/1994 | Garfield | ............... | A61H 31/007 128/205.13 |
| 5,383,448 A * | 1/1995 | Tkatchouk | ........ | A61M 16/0045 128/200.24 |
| 5,850,833 A * | 12/1998 | Kotliar | ................... | A61G 10/00 128/202.12 |
| 5,924,419 A * | 7/1999 | Kotliar | ................. | A23L 3/3418 128/200.24 |
| 6,126,721 A * | 10/2000 | Nemser | ................ | A61M 16/10 95/54 |
| 7,011,092 B2 * | 3/2006 | McCombs | ........ | A61M 16/0045 128/205.11 |
| 2002/0024155 A1 * | 2/2002 | Kusano | ..................... | F24F 6/04 261/104 |
| 2005/0072429 A1 * | 4/2005 | Kroll | ..................... | A61M 16/10 128/205.27 |
| 2006/0185669 A1 * | 8/2006 | Bassovitch | ........... | A61M 16/12 128/202.12 |
| 2007/0181128 A1 * | 8/2007 | Stroetz | ................ | A61M 16/12 128/204.22 |
| 2007/0221225 A1 | 9/2007 | Kutt | | |
| 2008/0196726 A1 | 8/2008 | Brown | | |
| 2011/0212811 A1 | 9/2011 | Rutten | | |
| 2012/0272956 A1 | 11/2012 | Rusher | | |
| 2012/0295765 A1 | 11/2012 | Foley | | |

* cited by examiner

Theoretical calculation of $O_2$ partial pressure when both inhalation and exhalation gas flow through the oxygenator at rates of 1500 ml/min, 2000 ml/min, and 2500 ml/min.

- - - - - QG = 1500 ml/min
——— QG = 2000 ml/min
- - - - - QG = 2500 ml/min

Fig. 9

Theoretical calculation of $CO_2$ partial pressure when both inhalation and exhalation gas flow through the oxygenator at rates of 1500 ml/min, 2000 ml/min, and 2500 ml/min.

- - - - - QG = 1500 ml/min
——— QG = 2000 ml/min
- - - - - QG = 2500 ml/min

Fig. 10

Theoretical calculation of $O_2$ partial pressure when only the exhalation gas flows through the oxygenator at rates of 1500 ml/min, 2000 ml/min, and 2500 ml/min.

- - - - - - QG = 1500 ml/min
———— QG = 2000 ml/min
— — — QG = 2500 ml/min

Fig. 11

Theoretical calculation of $CO_2$ partial pressure when only the exhalation gas flows through the oxygenator at rates of 1500 ml/min, 2000 ml/min, and 2500 ml/min.

- - - - - - QG = 1500 ml/min
———— QG = 2000 ml/min
— — — QG = 2500 ml/min

Fig. 12

Theoretical calculation of $O_2$ partial pressure when both inhalation and exhalation gas flow through the oxygenator at rates of 1500 ml/min, 2000 ml/min, and 2500 ml/min.

- - - - - - QG = 1500 ml/min
——— QG = 2000 ml/min
- - - - - QG = 2500 ml/min

Fig. 13

Theoretical calculation of $CO_2$ partial pressure when both inhalation and exhalation gas flow through the oxygenator at rates of 1500 ml/min, 2000 ml/min, and 2500 ml/min.

- - - - - - QG = 1500 ml/min
——— QG = 2000 ml/min
- - - - - QG = 2500 ml/min

*Fig. 14*

Theoretical calculation of O₂ partial pressure when only the exhalation gas flows through the oxygenator at rates of 1500 ml/min, 2000 ml/min, and 2500 ml/min.

- - - - - - QG = 1500 ml/min
———— QG = 2000 ml/min
– – – – QG = 2500 ml/min

*Fig. 15*

Theoretical calculation of CO₂ partial pressure when only the exhalation gas flows through the oxygenator at rates of 1500 ml/min, 2000 ml/min, and 2500 ml/min.

- - - - - - QG = 1500 ml/min
———— QG = 2000 ml/min
– – – – QG = 2500 ml/min

DEVICE AND METHOD FOR PERFORMING RESPIRATORY TRAINING

CROSS REFERENCE TO RELATED APPLICATIONS

This application is the US-national stage of PCT application PCT/EP2014/000305 filed 5 Feb. 2014 and claiming the priority of German patent application 102013001913.3 itself filed 5 Feb. 2013.

FIELD OF THE INVENTION

The invention relates to an apparatus for respiratory training, in particular altitude training, comprising a mouthpiece through which a person is able to exhale respiratory gas into or inhale respiratory gas from a closed space, and the closed space is formed at least in part by a container of variable volume and connected to the mouthpiece.

Furthermore, the invention also relates to a method of performing respiratory training, in particular altitude training, where a person exhales into a training apparatus through a mouthpiece and inhales from this training apparatus, in particular where an above-described apparatus can be used to perform the method.

BACKGROUND OF THE INVENTION

In the prior art, it is known, for example, that athletes perform respiratory training under a reduced oxygen partial pressure that simulates training at a higher elevation as so-called altitude training in order to increase athletic performance at lower elevations. Positive effects are based substantially on the body's adaptive response under hypoxic conditions, so that such training performed under a reduced $O_2$ partial pressure can have a physically as well as mentally positive influence on performance.

The simulation of respiration at high altitude is here basically achieved by setting a reduced $O_2$ partial pressure in the respiratory gas intended to be inhaled, as compared to such pressure at conventional elevations such as, for example, at sea level.

Instead of actually training at the corresponding altitude, the desired outcome can be achieved with an apparatus of the above-described kind, with which a person who is training exhales respiratory gas into a closed space and inhales it from this closed space, so that the inhaled inspiration gas is composed at least in part of the exhaled respiratory gas and the $O_2$ partial pressure is therefore lowered by the oxygen consumption of the person breathing. The prior art therefore includes a kind of pendulum breathing, during which the person breathing always inhales back a part of the exhaled respiratory gas (expiration gas).

Here, one speaks of respiratory gas instead of breathing air because the term "air" suggests a fixed, specific gas composition, but this in fact changes with the apparatus relative to the composition of normal air, especially with respect to the partial pressures of oxygen and carbon dioxide.

For this purpose, the apparatus known in the prior art has a closed space that is formed at least in part by a variable-volume container provided on a mouthpiece, for example, a mouthpiece that is to be taken into the mouth or even a mask that is to be worn. Selecting the size of the container volume makes it possible to influence the total closed space of such an apparatus, and thus to also influence the proportion of the exhaled respiratory gas (expiration gas) that is inhaled back by the person who is training. Selecting the container volume therefore makes it possible, with the apparatus of the prior art, to adjust the $O_2$ partial pressure at which the person training performs the respiratory training, e.g., altitude training.

The respiratory training made possible thereby or a method of performing the method, in particular with the above-described apparatus, preferably entails such a method as is not performed by a person for therapeutic purposes, but rather preferably only for the purpose of enhancing athletic performance.

The apparatus or method previously known in the prior art for performing such respiratory training, for example altitude training has a disadvantage in that, although the oxygen partial pressure can be influenced by altering the container volume or the total closed space of a corresponding apparatus (in particular, the oxygen partial pressure can be reduced by increasing the closed space), the result of so doing, in connection with this change of the oxygen partial pressure, is that the $CO_2$ partial pressure in the respiratory gas within the above-described closed space and thus in the respiratory gas that is to be inhaled (inspiration gas) is influenced simultaneously as well, and in particular such that, with the increase of the container volume and thus the decrease of the $O_2$ partial pressure, an increase of the $CO_2$ partial pressure is set, which has adverse effects on the body of the person training.

An apparatus has therefore also become known by which the process of inhalation takes place through a filter that is filled with an absorber material in order to absorb $CO_2$ from the inhaled air. However, this is problematic in that fine dust in the absorber could potentially reach the lungs of the person training, with potentially negative effects or even as a result of a considerable breathing resistance produced by the filters intended to be used, especially those that prevent the entry of particulate matter.

The absorption of the exhaled $CO_2$ is a time-dependent quantity, such that the $CO_2$ partial pressure ($CO_2$ concentration) in the respiratory gas (inspiration gas) is also time-dependent. Once the absorption efficiency is no longer 100%, then the $CO_2$ concentration in the respiratory gas (inspiration gas) rises in an undefined manner.

There are also specific uses in which, in addition to adjusting a specific $O_2$ partial pressure, it is desired to also adjust a specific $CO_2$ partial pressure that cannot be achieved with the conventional apparatus of the prior art, for lack of an explicit controllability, especially of the $CO_2$ partial pressure.

OBJECTS OF THE INVENTION

It is therefore an object of the present invention therefore to provide an apparatus of the above-described generic kind, as well as a method of performing respiratory training, in particular altitude training that open up the possibility of specifically adjusting the $O_2$ partial pressure and/or the $CO_2$ partial pressure in the respiratory gas to be inhaled (inspiration gas) by a person training.

Another object of the invention is to provide a method of and apparatus for respiratory training with which substantially any elevation can be simulated without further risks for the person training.

SUMMARY OF THE INVENTION

According to the invention, this object is solved by an apparatus of the above-described generic type, where the volume, formed at least in part by a variable-volume container connected to a mouthpiece, furthermore has one wall formed by at least one gas-permeable membrane and on whose outer side at least one gas-exchange chamber is provided so that this design according to the invention offers the possibility of influencing the $CO_2$ and/or $O_2$ partial pressure of the respiratory gas in the closed space through the at least one gas-permeable membrane, by gas exchange thereby taking place with a fluid in the gas-exchange chamber.

For this purpose, an apparatus according to the invention may be designed so that the mouthpiece through which a person inhales and exhales and that is configured, for example, as a mouthpiece to be taken into the mouth or is located in a mask covering the face is connected to the container of variable volume, and, in addition to the closed space of the variable-volume container, the total internal closed space is also formed by supply conduits or tubes between the mouthpiece and the container, as well as optionally by other elements provided on the apparatus that form the internal closed space, such as, for example, a gas exchange region that is provided opposite the above-described gas-exchange chamber on the other side of the at least one gas-permeable membrane and thus is also located inside the volume or forms a part of the total internal closed space.

It is irrelevant to the functioning of the apparatus whether, for example, with respect to an exhalation process, the at least one gas-permeable membrane is provided upstream of the container or downstream of the container, although according to the invention, the apparatus is preferably one where the at least one gas-permeable membrane is positioned upstream of the container of variable volume, in the direction of flow of the exhaled respiratory gas.

This means that when exhaling the respiratory gas through the mouthpiece and through a connecting conduit or tube region, a person breathes into a closed compartment of the apparatus where the at least one above-described gas-permeable membrane is provided; the respiratory gas flows over this at least one gas-permeable membrane, allowing a gas exchange of oxygen and/or carbon dioxide to take place; and the exhaled respiratory gas then arrives at the container of variable volume.

In contrast to the apparatuses and methods previously known in the prior art, this embodiment is advantageous in that the $O_2$ partial pressure and/or the $CO_2$ partial pressure is substantially influenced by gas exchange through the at least one gas-permeable membrane, thus making it possible to perform the desired altitude training or training under a specific $O_2$ partial pressure that has been reduced relative to sea level, and in particular under reproducible, adjustable conditions.

These reproducible, adjustable conditions arise primarily from the fact that the gas exchange can be influenced by the flow velocity or closed-space flow of the gas-exchange fluid on the side of the gas-exchange chamber that is traversed by the fluid. Such a gas-exchange fluid may be, for example, a gas, but in principle may also be a liquid.

The intensity of the gas exchange and thus the immediate influence of the partial pressures of $O_2$ and $CO_2$ can thus be significantly adjusted by the flow velocity or closed-space flow rate of the fluid used.

Here, preferably active flow through the gas-exchange chamber is effectuated by the fluid provided, for example, by a drive, preferably one that is built into the apparatus and with which the fluid can be pumped through the gas-exchange chamber. Such a drive may be, for example, an electric motor drive or else be operated by the respiratory gas flow of the inhaled and exhaled respiratory gas of a person training, so that an external power supply is not needed. Such a drive may be achieved, for example, by the changing pressure conditions in the container or even by a change in closed-space volume and the resulting mechanical movement of a section that moves with the change in closed space.

With the apparatus or the method according to the invention, in the simplest case, a single gas-permeable membrane is provided for the gas exchange, the respiratory gas that has been exhaled and/or is to be inhaled flows on one side of this gas-permeable membrane, and the gas-exchange fluid flows on the other side of this gas-permeable membrane. The closed-space flow of the fluid may come from, for example, a person training through athletic activities (driving a ventilator by muscle power).

However, should the surface made available for the gas exchange with such a membrane be too small, then it is also possible to provide a preferred development where the closed space surrounds the respective outer surfaces of a plurality of gas-permeable tubular fibers, through the inside of each of which a gas-exchange fluid and in particular for the $CO_2$ or $O_2$ gas exchange, is able to flow, in particular wherein such a plurality of gas-permeable tubular fibers can be formed by a tubular fiber bundle.

The closed space of an apparatus according to the invention where such gas-permeable tubular fibers are located can therefore be formed, for example, by a so-called "oxygenator," as is used for ventilation, for example in heart-lung machines. Such an oxygenation is typically provided in a housing that comprises two closed spaces separated by the gas-permeable tubular fibers, and one closed space and, in particular, the one that adjoins the outer surface of the tubular fibers, is part of the above-described total internal volume according to the invention, and the other closed space region is for the fluid doing the gas exchange. Gas-permeable membranes or tubular fibers that are suitable for the gas exchange may be made of, for example, polymethylpentene, silicone, or polypropylene.

Selecting different $O_2/CO_2$ permeability ratios of the membranes (tubular fibers) used makes it possible to adjust different $O_2$ and $CO_2$ transfer rates, and thus different $O_2$ and $CO_2$ partial pressures (concentrations) in the apparatus according to the invention.

An embodiment of the invention may also have the plurality of gas-permeable tubular fibers formed by a modularly assemblable mount in which at least one module having a plurality of tubular fibers can be used, preferably in which at least two modules, each having a plurality tubular fibers, can be used.

In such a mount that forms a gas exchanger, the above-described closed space adjoins the gas-exchange chamber via the at least one module. The modularity makes it possible to easily adjust a desired transfer rate through the selection of a specific module or plurality of specific, and/or mutually different modules, each of a plurality of tubular fibers.

The $O_2$ and $CO_2$ transport in the gas exchanger and the membrane surface thereof can thus be influenced and adjusted, and thus so too can the $O_2$ and $CO_2$ partial pressures (concentrations) in the inspiration gas be influenced and adjusted.

An embodiment may also provide for equipping the tubular fibers with a $CO_2$ absorber, for example, in the walls of the tubular fibers, with a modular design, it would be possible, for example, for a module to comprise such absorbent tubular fibers, and in particular to be completely formed solely of absorbent tubular fibers. Such a module or plurality of such absorbent modules may be used, for example, together with one or more non-absorbent modules in the above-described gas exchanger. This then results in the possibility of further reducing the $CO_2$ partial pressure in the apparatus, and even optionally of completely eliminating $CO_2$.

In one embodiment of the apparatus that provides a drive, as previously described, in particular in the further design with a plurality of gas-permeable tubular fibers, an active pumping of the gas-exchange fluid through the interior of the tubular fibers, as previously described, is generated by such a drive, for example, by an electric motor, or even driven by the respiratory gas flow of inhaled and exhaled respiratory gas.

With the apparatus or method according to the invention, the container volume of the above-described container is adjustable, to which end the container may be formed in a possible embodiment, for example as a variable-length bellows, or to be formed with at least two container parts that telescope relative to one another. There is thus the possibility of designing the total internal volume according to the invention so as to be variable by changing the volume of the container used, and of making usage-specific adjustments.

In connection with the apparatus according to the invention and in contrast to the prior art, it should be taken into account that according to the invention, the size of the container volume is at least substantially if not totally irrelevant for the adjustment of the respective partial pressures, because according to the invention, the desired partial pressures of $O_2$ and/or $CO_2$ are adjusted by the gas exchange that takes place through the gas-permeable membrane.

Instead, the size of the container and thus the size of the total internal volume in a method according to the invention for respiratory training, in particular altitude training, cause there to be adjustments to the number of respirations or time after which the desired partial pressure is achieved.

The method according to the invention for respiratory training, such as altitude training and in particular in connection to the above-described apparatus, provides that with the number of respirations, the $O_2$ and/or $CO_2$ partial pressure in the closed space of the training apparatus asymptotically approaches a final value, and the size of the final value is adjusted by the size of the closed space flow of the gas-exchange fluid through the gas-exchange chamber that comprises the at least one above-described membrane.

This is particularly the case with the apparatus according to the invention that has a total internal closed space that is sealed from the environment, even though it may also be provided according to the invention, in the design of the apparatus, to design the internal volume so as to be open to the external environment, for example through an opening in the container, so that an additional air exchange with the environment can also take place.

The apparatus according to the invention, especially when the internal closed space or the container is closed to the ambient air, has an advantage in that even untrained individuals can immediately begin respiratory training with such an apparatus, thus providing the possibility of having the course of the asymptotic approximation to the final value of partial pressure be adapted to the untrained individual, through the container volume, and in particular so that this final value is achieved comparatively slowly compared to a smaller selection for the container volume or the total volume for a trained person, with whom the final partial pressure can be achieved more quickly.

Thus, for example, the final partial pressure of $O_2$ or $CO_2$ is achieved more quickly with a relatively small container closed space or total volume, and there is a slower asymptotic approximation of the final pressure with the opposite, comparatively larger internal closed space or container closed space.

In an embodiment according to the invention in which the internal volume or the container that contributes significantly to the internal volume is closed to the ambient air, then for the purpose of further development it is possible to provide that a so-called breath-gas reservoir forms a part of the closed space, in particular a breath-gas reservoir that directly adjoins an adjustable container and in particular is provided downstream of the container in the direction of flow of the exhaled air, and this breath-gas reservoir comprises movable and/or flexible wall regions so that the volume of the breath-gas reservoir can be enlarged and diminished through inflowing and outflowing respiratory gas.

Thus, such an embodiment takes into account the fact that with an internal closed space that is closed against the ambient air, this closed space should not be constant, because otherwise the pressure in the apparatus would rise with the exhalation of air, thus bringing increased resistance against the process of exhalation.

Instead, it is desirable for a person training to always be able to train with the same breathing resistance, so that in order to achieve this objective, such a breath-gas reservoir is provided that enlarges or diminishes its own closed space through the inflowing and outflowing air, due to the fact that a resulting pressure or closed space increase causes movement of the movable or flexible wall regions that, for example, may be formed of an elastic membrane or a movable film, whereby the increase in volume of the closed space holds the pressure in the apparatus at substantially the same level.

Here, a further development may provide that movement and thus the maximum closed space that a breath-gas reservoir can take can be limited, and in particular can be variably limited by at least one adjustable stop such that the movable or flexible wall regions of the breath-gas reservoir can engage upon maximum filling with respiratory gas. Such a stop may thus involve, for example, a housing region that is, for example, perforated and into which the flexible wall regions, for example a movable film or a flexible membrane fits and comes into contact with the perforated wall regions, thus preventing further movement of these movable wall regions and limiting the maximum closed space.

Such a breath-gas reservoir that preferably is adjustable in terms of the maximum volume of its closed space according to the above-described embodiment, may preferably be adjusted during the performance of the training such that the closed space occupied by the breath-gas reservoir out of the total volume corresponds to the so-called breath closed space of the person training, and so thus substantially corresponds to the amount of respiratory gas that a person moves when inhaling and exhaling and that thus corresponds at least substantially to the maximum lung closed space.

Here, however, in another development, it is possible to provide that at the closed space and in particular at the variable-volume container or at the breath-gas reservoir, there is at least one valve provided through which respiratory gas can be released from the closed space to the external environment if there is a positive pressure relative to the environment, and/or there is at least one valve provided through which fresh air can be drawn into the closed space if there is a negative pressure relative to the external environment.

Doing so makes it possible, in particular, to take into account the fact that the maximum volume of the breath-gas reservoir is optionally selected so as to be smaller than the breathing closed space of the person training, so that in such a case, if the person, when exhaling, blows a greater closed space into the apparatus according to the invention than the breath-gas reservoir is able to receive, this excess exhaled respiratory gas (expiration gas) is released out to the external environment via the valve and, in the reverse case, if the person inhales more respiratory gas (inspiration gas) than the breath-gas reservoir makes available at the variable closed space fraction, then the resulting negative pressure causes fresh air to be drawn in from the environment via the at least one valve.

This ensures, in both cases, that there is no possible instance in which the apparatus according to the invention might be a source of resistance against the process of breathing during the respirations of a person training.

One possible embodiment according to the invention may provide that in the process of both exhalation and inhalation, the flowing respiratory gas flows past the at least one gas-permeable membrane, in particular the plurality of gas-permeable tubular fibers, so that gas exchange of $O_2$ and/or $CO_2$ can take place in both of these periodically repeating respiratory movements.

Another embodiment may also provide that the moving respiratory gas within the apparatus according to the invention flows past the at least one membrane for the purpose of the gas exchange either only during exhalation or only during inhalation.

Here, it may be provided that at least one one-way valve and at least one bypass conduit provide a bypass route for the other direction of flow, so that the air flowing in the other direction is not guided past the at least one gas-permeable membrane. In particular, it may be provided that only the respiratory gas (expiration gas) that is blown into the apparatus during exhalation flows over the at least one gas-permeable membrane, and at least one one-way valve and a bypass line ensure that on inhalation, the respiratory gas bypasses gas exchange and is fed directly to the mouthpiece from the variable-volume container and/or from the breath-gas reservoir.

BRIEF DESCRIPTION OF THE DRAWING

Embodiments and characteristics of the method according to the invention are described below. In the drawing.

SPECIFIC DESCRIPTION OF THE INVENTION

Figure 1:
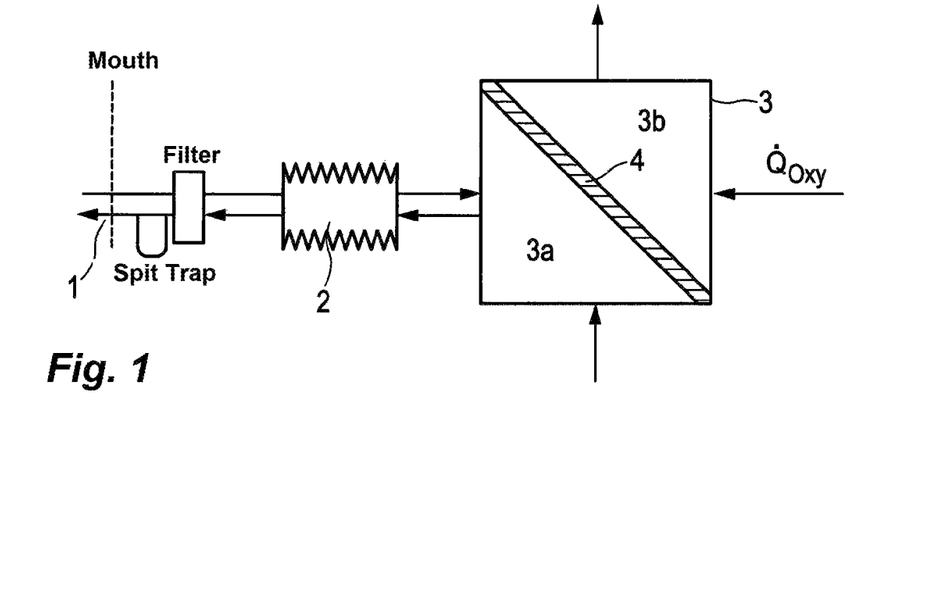
FIG. 1 is a schematic view of a first embodiment of the system of this invention.

FIG. 1 illustrates a principal schematic representation of an apparatus according to the invention for carrying out the method according to the invention where a person (not shown) breathes through a mouthpiece 1 (only schematically illustrated), blowing respiratory gas into the apparatus according to the invention or inhaling respiratory gas out of the apparatus according to the invention that, according to the schematic drawing shown here, comprises a container 2 of variable volume as well as a gas exchanger 3 having an internal closed space that is subdivided into closed compartments 3a and 3b by at least one gas-permeable membrane 4, the closed compartment 3a being connected to the total internal volume according to the invention and the closed compartment 3b being a gas-exchange chamber through which a gas-exchange fluid is passed.

The inhaled and exhaled respiratory gas is therefore here passes over the at least one gas-permeable membrane 4 in order to thus allow a gas exchange to take place with the fluid flowing on the other side of the at least one membrane, so that the flow velocity or closed space flow of this fluid makes it possible to adjust the ultimately attained $O_2$ or $CO_2$ partial pressure inside the apparatus according to the invention.

As has already been described above, the size of the volume of the container 2 of variable volume is selected so as to influence the total internal volume according to the invention that is thus composed at least of the internal closed space of the container 2, the closed space 3a of the apparatus 3 provided for the gas exchange, and optionally additional elements connecting these parts, such as conduits or tubes or other such components of the overall apparatus according to the invention that conduct the respiratory gas.

FIG. 1 shows the variable-volume container 2, for example, as a bellows upstream in the direction of flow of the exhaled respiratory gas (expiration gas) of the gas exchanger having two closed compartments 3a and 3b and the at least one gas-permeable membrane. Even while achieving substantially the same function, the container 2 may also be provided downstream in the direction of flow of the exhaled respiratory gas of the apparatus 3 provided for the gas exchange, as shown in the FIG. 2 as an alternative (without showing the mouthpiece), in which the total volume according to the invention is open toward the environment via to the container 2 that here has an opening 2a to the environment.

Figure 2:
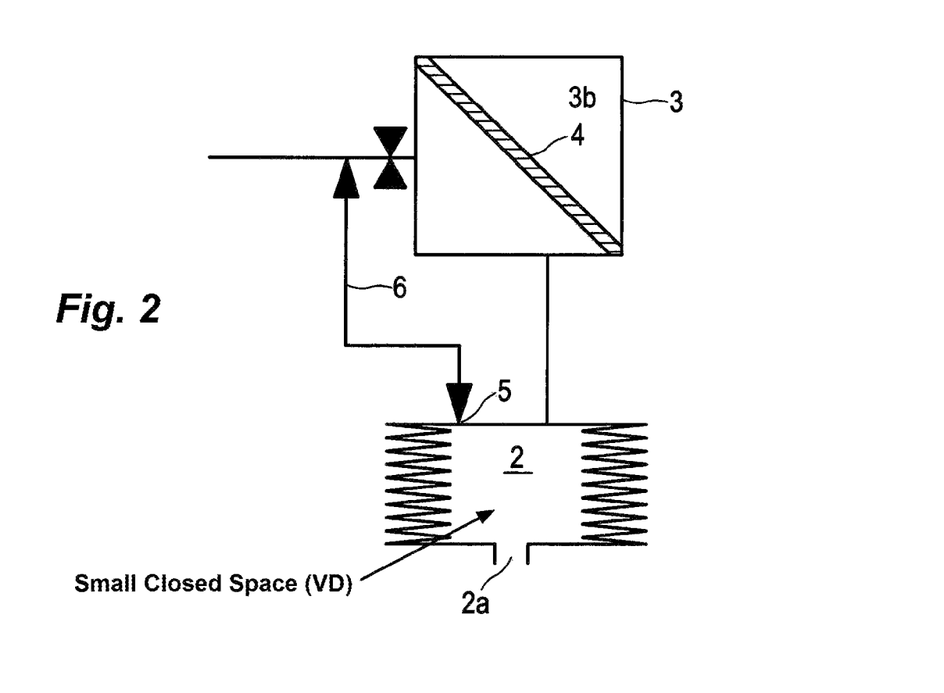
FIG. 2 is a detail of the first embodiment of FIG. 1.

The exhaled respiratory gas (expiration gas) can therefore also escape to the ambient air, and likewise a person is able to inhale ambient air through the entire apparatus when inhaling. FIG. 2 also illustrates a variant embodiment where the matter of whether respiratory gas should be guided past the at least one gas-permeable membrane 4 via the bypass line 6 only upon exhalation or only upon inhalation can be adjusted depending on the direction of one-way valves 5 (not shown), and thus a gas exchange with the fluid in the closed space region 3b of the apparatus part 3 always takes place only in one of the two respiratory phases (inhalation or exhalation).

Figure 3:
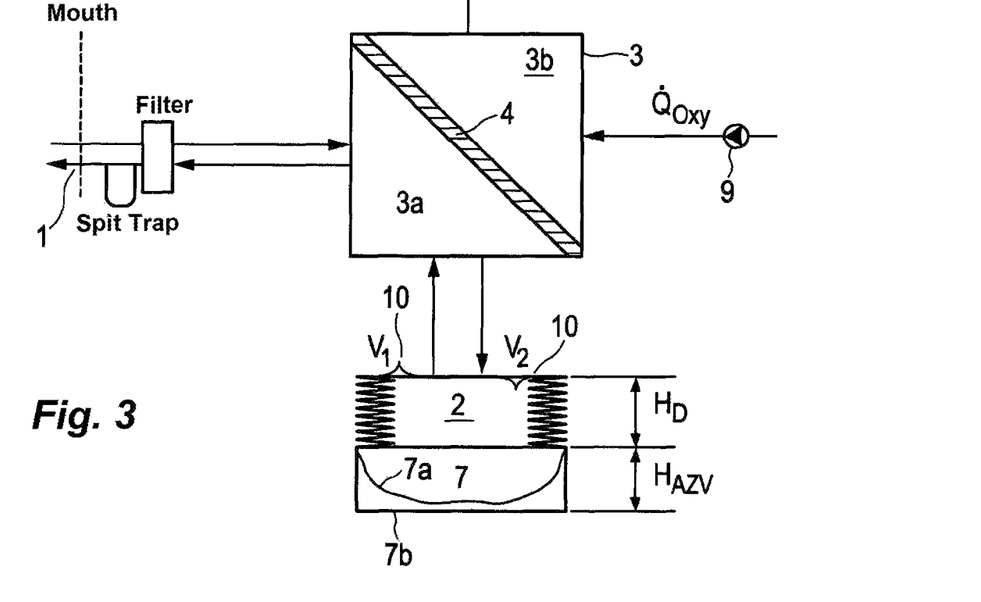
FIG. 3 is a view like FIG. 1 of a second embodiment of the system of this invention.

Yet another embodiment of the apparatus according to the invention or the performance of the method is shown in FIG. 3 that, in contrast to FIGS. 1 and 2, illustrates that first the volume-variable container 2 is provided downstream in the direction of flow of the exhaled respiratory gas (expiration gas) of the gas exchanger 3, and a breath-gas reservoir 7 is also provided on the container 2 and is part of the total internal volume according to the invention, comprising a movable and/or flexible wall regions 7a, for example, due to being formed as a movable film or as a movable elastic membrane, so that the volume of the breath-gas reservoir 7 can get larger or smaller by the inflow and outflow of the respiratory gas, and FIG. 3 further illustrates that the maximum volume of the breath-gas reservoir 7 is limited by a stop 7b formed by the outer walls of the breath-gas reservoir 7. This causes the movable wall regions 7a to follow the increase in closed space upon exhalation, until the wall regions come up against the limiting stop 7b and thus the volume of the breath-gas reservoir 7 can no increase no further.

Figure 4:
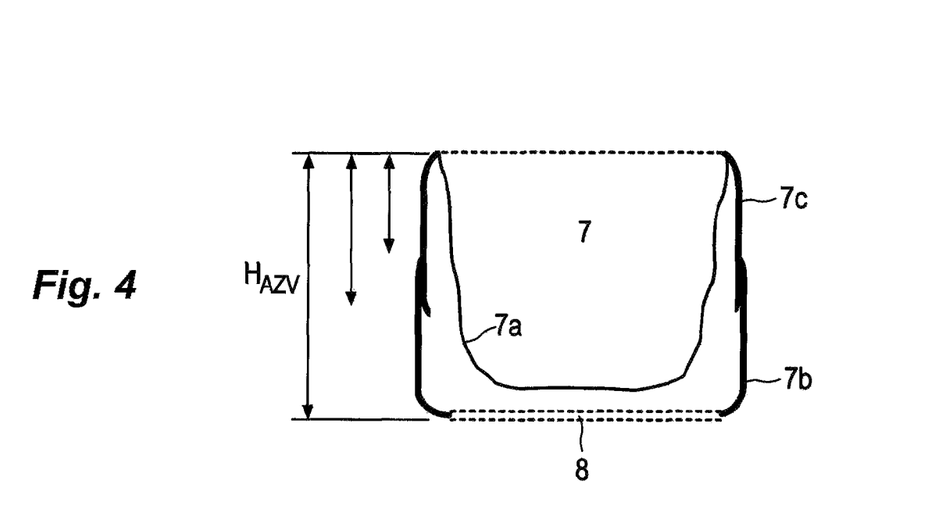
FIG. 4 is a graph illustrating operation of the second embodiment.

FIG. 4 illustrates a detail of the breath-gas reservoir 7 having the flexible wall regions 7 and the stop 7b, and showing in detail that the maximum closed space of this breath-gas reservoir 7 can be variably adjusted by displacement of the stop 7b and in particular by telescoping relative to another housing section 7c, for example, one that is fixed to the container 2. The design here could also be a bellows, like the container 2. At least one wall region of the housing wall serving as the stop 7b is here formed with perforations 8, so that upon expansion and thus with an increase in closed space, air outside the movable and/or flexible wall regions 7a can be displaced out of the housing of the breath-gas reservoir 7 and offers no resistance.

The embodiment according to FIG. 3 is such that both the inhaled respiratory gas and the exhaled respiratory gas flow over the at least one gas-permeable membrane 4, and therefore in both respiratory phases gas exchange can take place with the fluid in the closed space 3b, to which end a desired flow rate in the closed space of the gas-exchange fluid can be determined here with a drive 9. In this instance, the drive 9 may be an electric-motor drive, and in particular a pump.

FIG. 3 further illustrates that valves 10 may be provided in particular on the container 2, but optionally also on any wall region limiting the total volume according to the invention, the valves serving as one-way valves and, in the present instance, being used to release the exhaled respiratory gas (expiration gas) out to the environment if there is a resulting positive pressure within the apparatus upon exhalation, or to inhale ambient air into the apparatus if a negative pressure is created in the process of inhalation. These effects may in particular arise when the variably adjustable volume of the breath-gas reservoir 7 is adjusted so as to be smaller than the breathing closed space of the person training that may be, for example, the same as his or her lung volume.

Should a larger quantity of $CO_2$ be eliminated than the quantity of $O_2$ that is fed into the gas exchanger, the result is a deficit in the closed space in the apparatus over the course of use thereof. Here, then, air from the environment may optionally be drawn into the apparatus.

Figure 5:
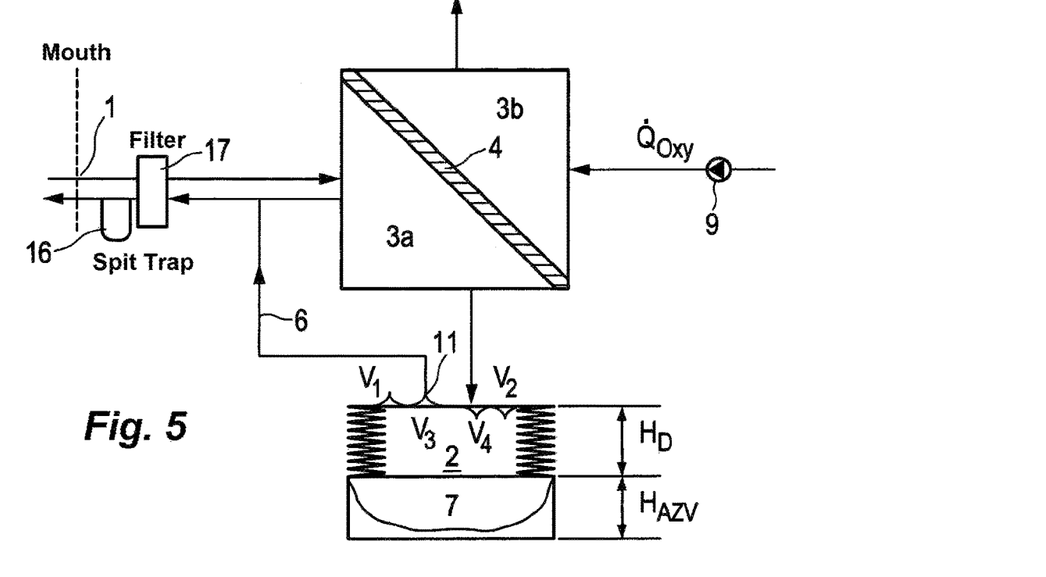
FIGS. 5, 6, and 7 are schematic views illustrating third, fourth, and fifth embodiments of the invention.

As an alternative to FIG. 3, FIG. 5 illustrates an embodiment where, as with FIG. 2, a bypass line 6 is provided that runs directly from the container 2 via a one-way valve 11 and causes the air to be directly guided to the mouthpiece 1 from the container 2 and from the breath-gas reservoir 7 during exhalation, bypassing the gas-permeable membrane 4. In the embodiment according to FIG. 5, therefore, a gas exchange only takes place upon exhalation, but not upon inhalation, when the exhaled respiratory gas (expiration gas) flows over the at least one gas-permeable membrane 4. The direction of the air flow inside the bypass 6 can also be reversed by appropriate orientation of the one-way valve 11.

Figure 6:
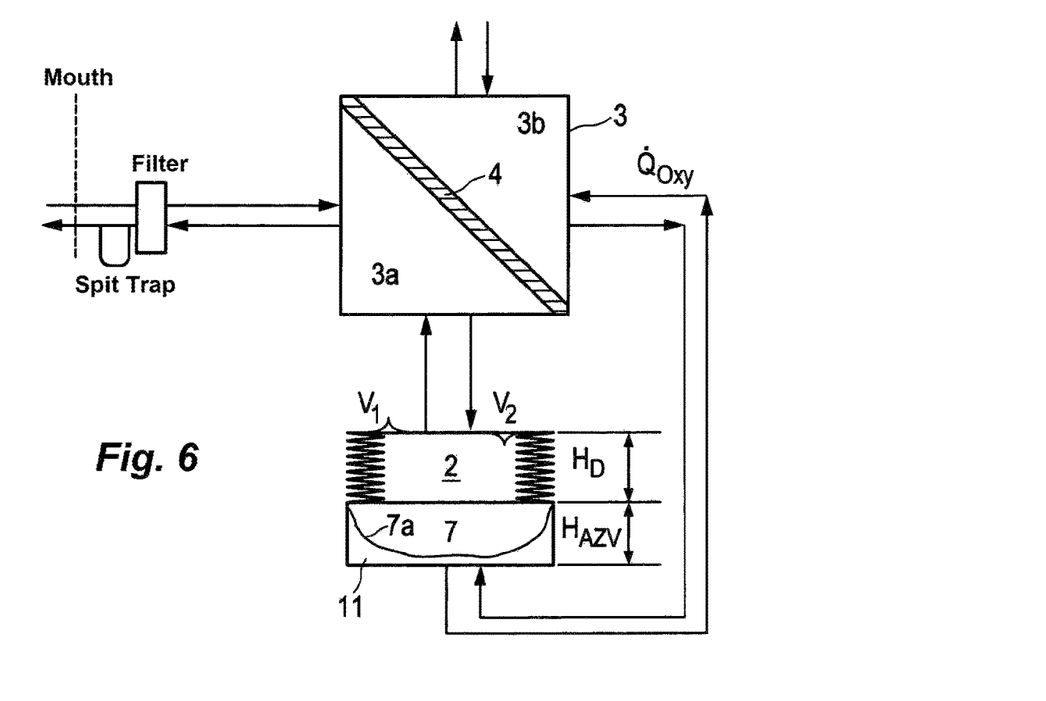

FIG. 6 illustrates yet another embodiment that in particular can be combined with those embodiments that comprise a breath-gas reservoir 7 and in which the internal closed space of the entire apparatus according to the invention is closed off from the environment. This embodiment makes clear that movement of the movable wall regions 7a in the breath-gas reservoir upon exhalation and inhalation reduces or enlarges the volume of the closed air space 11 on the other side, i.e. lying outside the internal volume according to the invention. The air or alternatively even any fluid that is displaced or drawn in through the closed space region 11 may also generate movement and closed space flow in the chamber section 3b of the gas exchanger 3, so that instead of an electric motor drive, the closed space flow of a gas-exchange fluid is also produced directly by the respiration of the person training on the one side of the at least one gas-permeable membrane 4.

Figure 7:
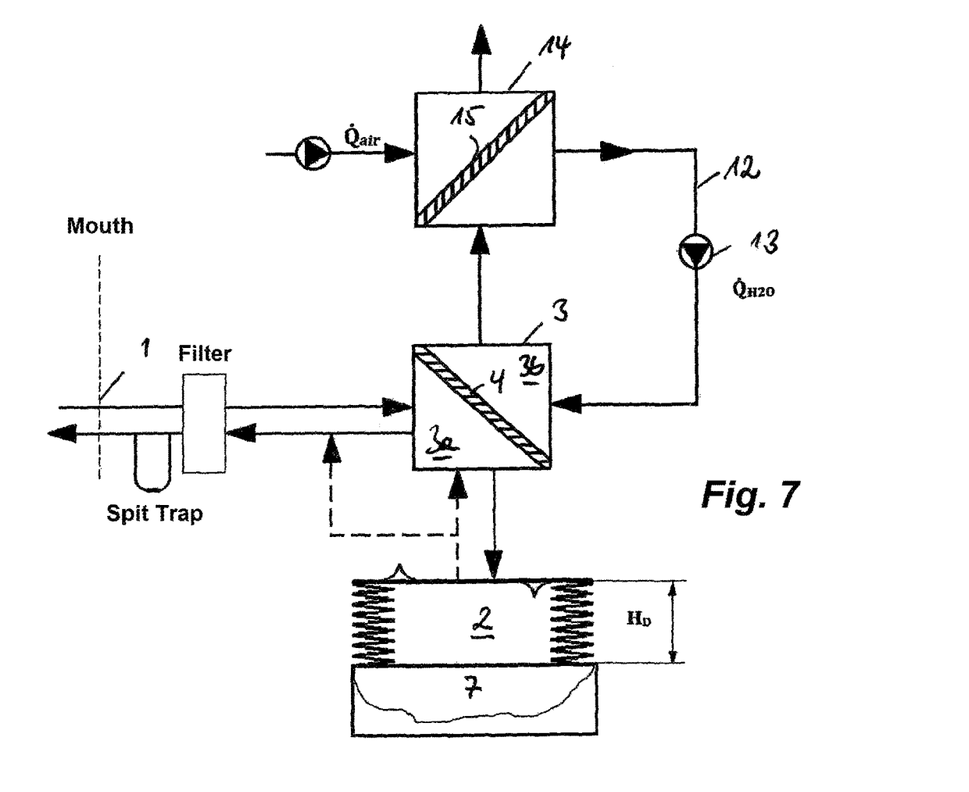

FIG. 7 illustrates another embodiment similar to those of the previous embodiments, and here, water is used as the gas-exchange fluid for the adjusting the partial pressures of $O_2$ and $CO_2$ in the internal volume according to the invention, the water being conveyed in a closed circuit 12, in particular by an electric motor drive 13, and within this circuit two gas exchangers are provided—one for adjusting the $O_2$ and $CO_2$ partial pressure in the internal volume according to the invention, and another gas exchanger 14 is provided, also with at least one gas-permeable membrane 15, in order to carry out the gas exchange between water within the circuit 12 and another fluid, for example air.

All of the embodiments of the drawings described above illustrate that a collection container 16, for example, for saliva from the mouth of the person training may be provided at the mouthpiece that, for example, is provided in the mouthpiece or in a mask covering the face, for moisture that has condensed inside the respiratory gas, a filter and in particular a gas filter 17 may optionally be provided, as well. These elements and a filter for collecting the gas moisture are not mandatory or essential for the method or apparatus according to the invention, and may also be eliminated in any of the embodiments shown.

Figure 8:
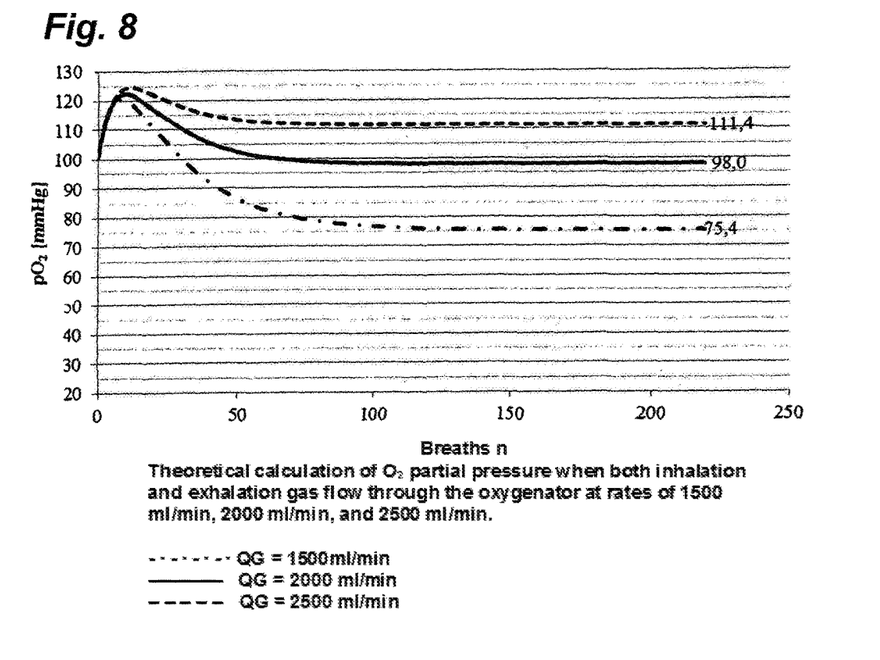
FIGS. 8-15 are graphs illustrating the invention.
Figure 9:
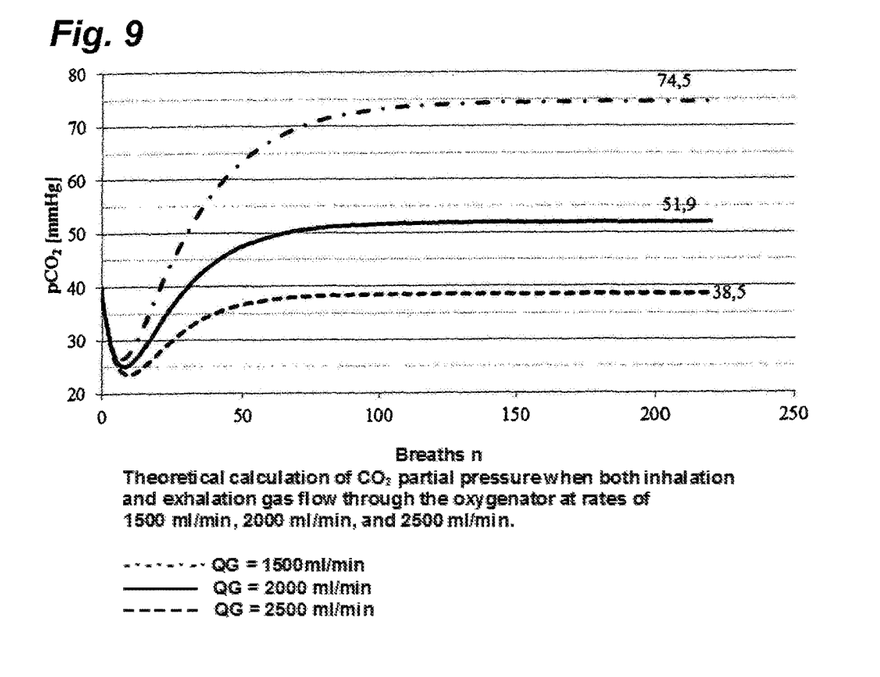

FIGS. 8 and 9 illustrate the evolution of the partial pressures of $O_2$ (FIG. 8) and $CO_2$ (FIG. 9) in differently adjusted flow rates of the gas-exchange fluid through the gas-exchanging chamber 3. Here it can be seen that the final partial pressure of $O_2$ or $CO_2$ in the interior space according to the invention can be adjusted in accordance with the closed space flow.

This final pressure is, in each case, shown with an asymptotic curve after a certain number of respirations n that are shown on the respective X-axis of each drawing. FIGS. 8 and 9 thus demonstrate that in comparison to the prior art, it is possible to reproducibly and adjustably select the training conditions for a person through the flow rate of the gas-exchange fluid, i.e. select the partial pressures that must be achieved for $O_2$ or $CO_2$ and thus also the altitude to be simulated during training.

FIGS. 8 and 9 show the typical progression of the partial pressure of $O_2$ and $CO_2$ for when the respiratory gas moving within the apparatus flows over the at least one gas-permeable membrane 4 of the apparatus upon both exhalation and inhalation.

Figure 10:
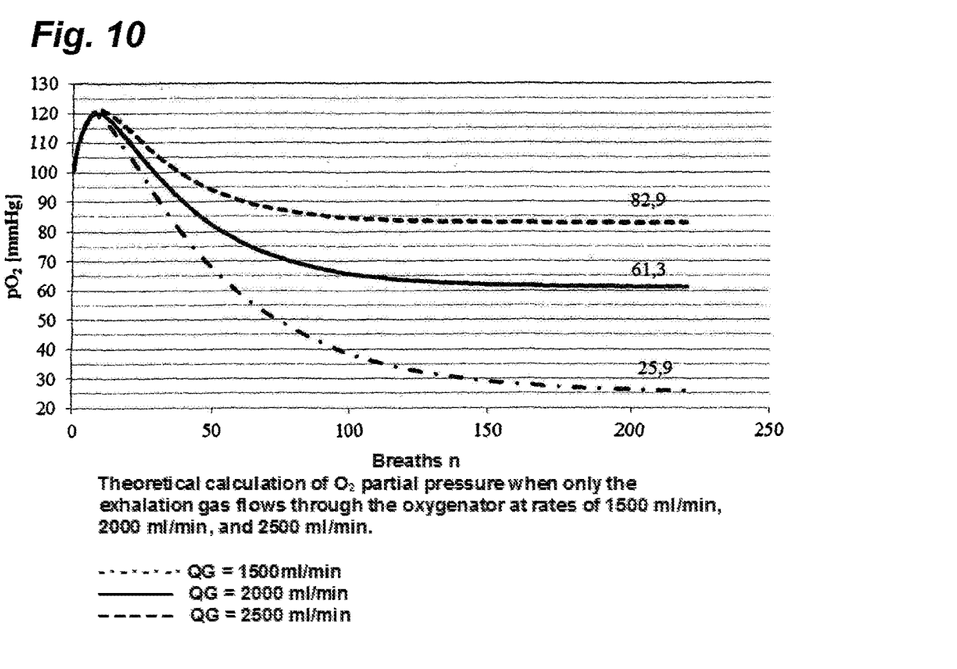
Figure 11:
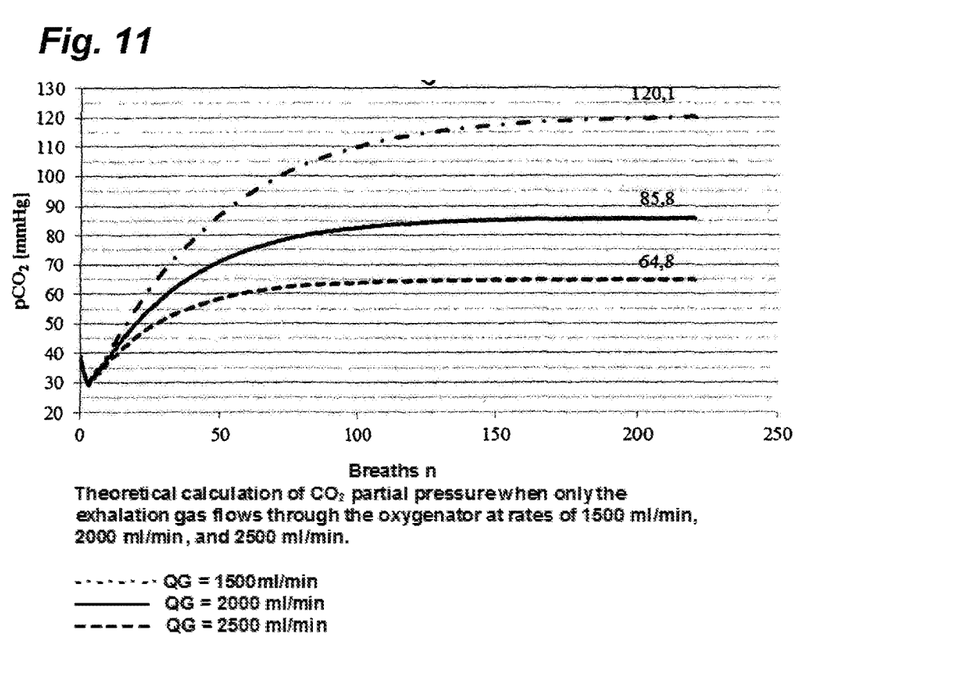

FIGS. 10 and 11 illustrate the same situation for the same flow rates of the gas-exchange fluid for a case in which the air moving in the apparatus is subject to a gas exchange (i.e. flows over the at least one gas-permeable membrane 4 only upon exhalation, while the inhaled respiratory gas (inspiration gas) flows directly to the mouthpiece via a bypass line and a one-way valve, as visualized, for example, in FIGS. 2 and 5.

Here it can be seen that at the same flow rates, with the oxygen partial pressure, a lower pressure is achieved in comparison to the two iterations of gas exchange, whereas with the $CO_2$ partial pressure, a higher pressure in comparison to the two iterations of gas exchange in FIGS. 8 and 9 is achieved. It is thus possible, therefor, to influence the respective partial pressures needing to be achieved for oxygen and $CO_2$, by selecting whether the air moving in the apparatus is subject to a gas exchange only upon inhalation, only upon exhalation, or upon both respirations.

Figure 12:
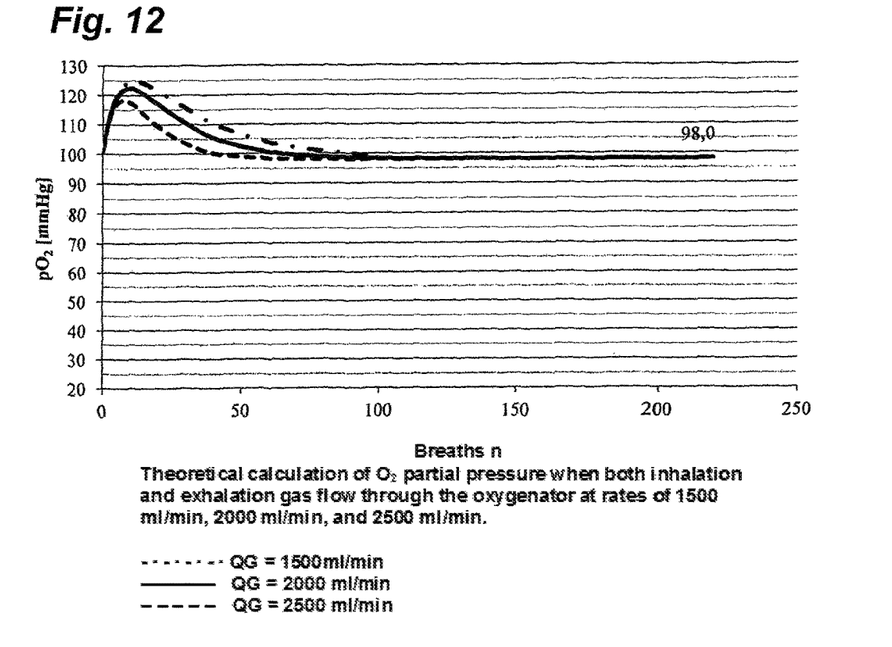
Figure 13:
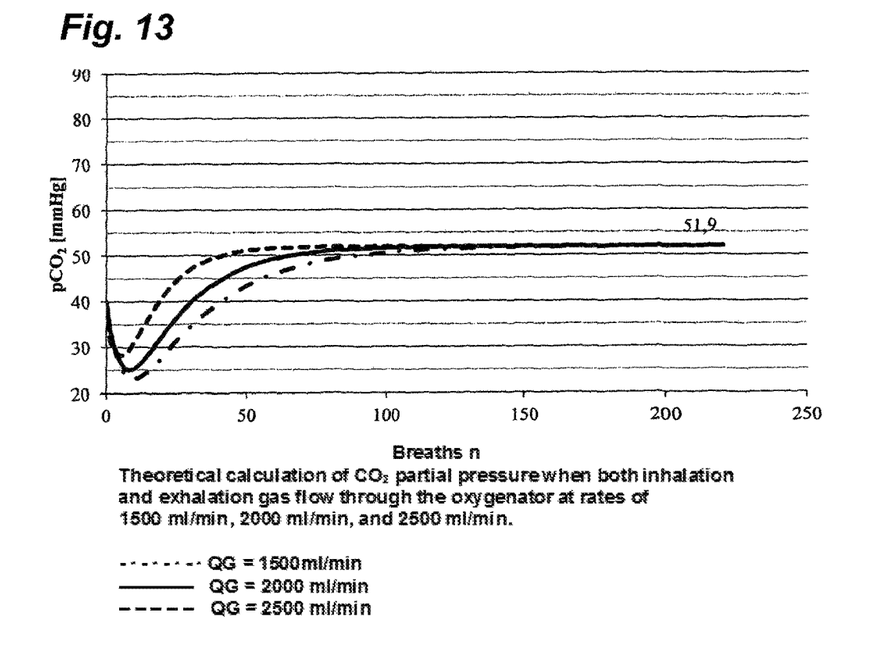

FIGS. 12 and 13 illustrate, in turn, the respective evolution of the partial pressures for $O_2$ and $CO_2$ as a function of the number of respirations and for different sizes of the total closed space of the respective apparatus according to the invention, these being selected here by differently adjusted container closed spaces of the above-described container 2. It can be seen here that the respective partial pressures of $O_2$ and $CO_2$ that are adjusted by the closed space flow of the fluids participating in the gas exchange, are achieved at different speeds in accordance with the volume or the container.

Figure 14:
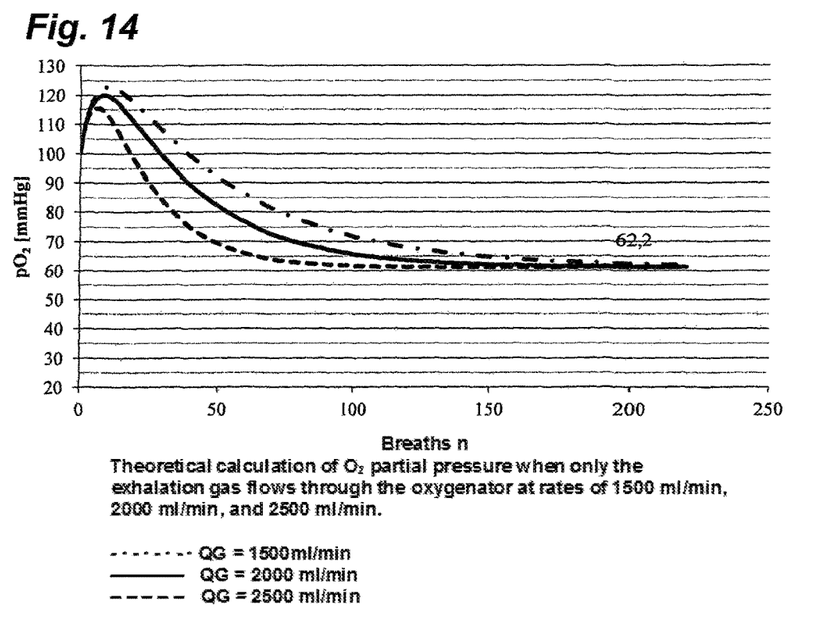
Figure 15:
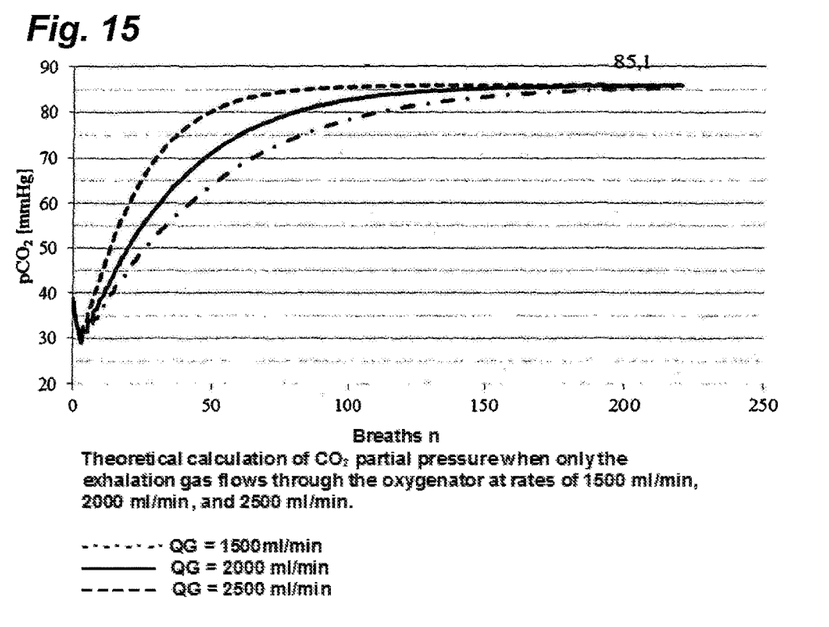

In this case, FIGS. 12 and 13 depict the case corresponding to FIGS. 8 and 9, where the respiratory gas (inspiration and expiration gas) flows over the at least one gas-permeable membrane upon both inhalation and exhalation. In contrast, FIGS. 14 and 15 illustrate the same case in which only the exhaled air is subject to a gas exchange, as has also been described for FIGS. 10 and 11.

Here, not only are the respectively achieved limit values changed, but also the dependence on the volume is significantly recognizable.

In particular, performing the method of training a person opens up the possibility of enabling an untrained person to train with a larger volume, so as to reach the adjusted final value of the oxygen or carbon dioxide partial pressure over a longer period of a time, than a trained person for whom the volume can be selected so as to be lower.

Regarding the apparatus schematically shown in FIGS. 1 to 7, it should be noted that a single gas-permeable membrane 4 is shown in the gas exchanger 3 and so only one membrane 15 is shown with the apparatus 14, solely for the purpose of simplifying the depiction, whereas in practice a bundle of a plurality of gas-permeable tubular fibers may preferably be provided, in particular tubular fibers having an exterior on which the respiratory gas flows and an interior on which the gas-exchange fluid acts.

With the same initial and boundary conditions, it is possible to measure different $O_2$ and $CO_2$ patterns (as a function of time) for different users. The apparatus can thus be used to evaluate the user's lungs.

The invention claimed is:

1. An apparatus for respiratory training, the apparatus comprising:
   a mouthpiece through which a person is able to exhale and inhale respiratory gas;
   a variable-volume container forming at least part of a closed space connected to the mouthpiece;
   at least one gas-permeable membrane delimiting a part of the closed space on one side and forming on an opposite side a gas-exchange chamber; and
   means operated by the respiratory gas flow of the inhaled and exhaled respiratory gas for flowing an $O_2$ or $CO_2$ gas-exchange fluid over the opposite side of the membrane.

2. The apparatus according to claim 1, wherein the container is closed to ambient air.

3. The apparatus according to claim 2, further comprising:
   a breath-gas reservoir forming part of the closed space immediately adjacent the variable-volume container, the breath-gas reservoir comprising movable or flexible wall regions so that the volume of the breath-gas reservoir can be made larger or smaller by inflowing and outflowing respiratory gas.

4. The apparatus according to claim 3, further comprising:
   means for limiting movement and thus a maximum volume of the breath-gas reservoir the limiting means including at least one adjustable stop against which the movable or flexible wall regions of the breath-gas reservoir can engage at maximum filling with the respiratory gas.

5. The apparatus according to claim 2, further comprising:
   a valve in the closed space so as to release respiratory gas through the valve out to the environment from the closed space when there is a positive pressure relative to the outside environment or to draw fresh air in through the valve to the closed space when there is a negative pressure relative to the outside environment.

6. The apparatus according to claim 1, wherein the closed space adjoins respective outer surfaces of a plurality of gas-permeable tubular fibers in the interior of which the $CO_2$ or $O_2$ gas-exchange fluid flows actively in use.

7. The apparatus according to claim 6, wherein the gas-permeable tubular fibers are formed by a modularly assemblable mount comprising at least one module having a plurality of the tubular fibers.

8. The apparatus according to claim 1, wherein the container is a variable-length bellows or comprises at least two container sections that telescope relative to one another.

* * * * *